United States Patent
Baik et al.

(10) Patent No.: US 8,768,115 B2
(45) Date of Patent: Jul. 1, 2014

(54) TERAHERTZ INTERACTION CIRCUIT WITH OPEN CAVITY PORTION

(75) Inventors: Chan-wook Baik, Yongin-si (KR); Ho-young Ahn, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 194 days.

(21) Appl. No.: 13/401,304

(22) Filed: Feb. 21, 2012

(65) Prior Publication Data

US 2013/0051724 A1 Feb. 28, 2013

(30) Foreign Application Priority Data

Aug. 23, 2011 (KR) ........................ 10-2011-0084060

(51) Int. Cl.
*G02B 6/12* (2006.01)
*H01J 25/24* (2006.01)
*H01P 3/20* (2006.01)
*B23K 31/02* (2006.01)

(52) U.S. Cl.
USPC ............................................. 385/15; 315/3.5

(58) Field of Classification Search
USPC .................. 385/2–14, 24, 125–129; 331/154; 216/20; 315/3.5
See application file for complete search history.

(56) References Cited

U.S. PATENT DOCUMENTS

| | | | | |
|---|---|---|---|---|
| 2,641,730 A * | 6/1953 | Touraton et al. | ................ | 315/3.5 |
| 2,959,707 A * | 11/1960 | Wilmarth | ........................ | 315/3.5 |
| 4,398,121 A | 8/1983 | Chodorow et al. | | |
| 4,409,519 A | 10/1983 | Karp | | |
| 4,792,814 A * | 12/1988 | Ebisui | ........................... | 343/786 |
| 6,587,626 B2 * | 7/2003 | Beguin et al. | .................. | 385/125 |
| 8,653,911 B2 * | 2/2014 | Kim et al. | ...................... | 333/239 |
| 2013/0020939 A1 * | 1/2013 | Kim et al. | ................ | 315/111.41 |

FOREIGN PATENT DOCUMENTS

| | | |
|---|---|---|
| JP | 2005175612 A | 6/2005 |
| KR | 100326958 B1 | 6/2002 |
| KR | 100403980 B1 | 10/2003 |
| KR | 1020060091319 A | 8/2006 |
| KR | 100771508 B1 | 10/2007 |
| KR | 101002357 B1 | 12/2010 |

OTHER PUBLICATIONS

Jun He et al., "Investigation of a Ridge-Loaded Folded-Waveguide Slow-Wave System for the Millimeter-Wave Traveling-Wave Tube", IEEE Transactions on Plasma Science, vol. 38, No. 7, Jul. 2010, pp. 1556-1562.

Jun He et al., "Linear Analysis of a W Band Groove-loaded Folded Wavegide Travelling Wave Tube", Physics of Plasmas 17, 113305, 2010, pp. 1-7.

* cited by examiner

*Primary Examiner* — Akm Enayet Ullah
(74) *Attorney, Agent, or Firm* — Sughrue Mion, PLLC

(57) ABSTRACT

A terahertz interaction circuit includes a waveguide through which electromagnetic waves pass, the waveguide having a folded shape and including a narrow open cavity portion; and an electron beam tunnel through which an electron beam passes, the electron beam tunnel penetrating through the waveguide.

15 Claims, 16 Drawing Sheets

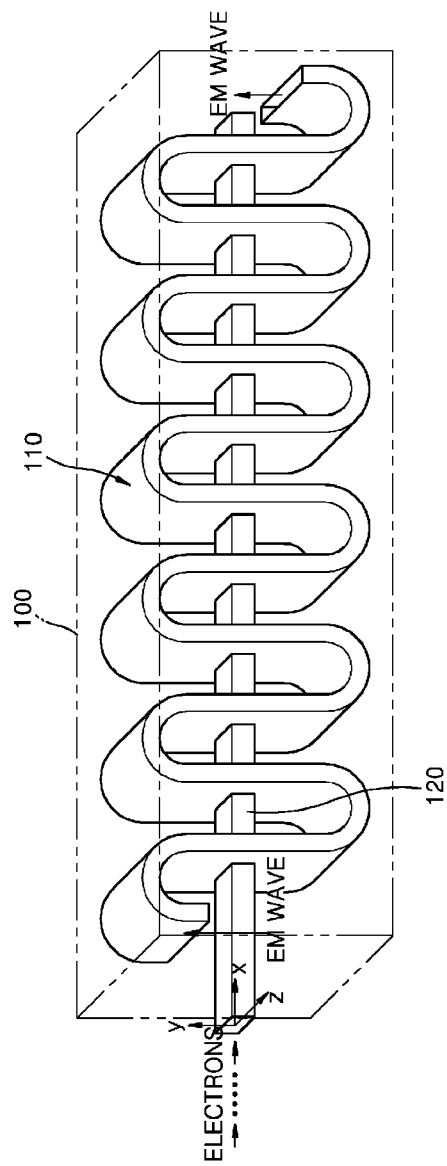

TERAHERTZ INTERACTION CIRCUIT WITH OPEN CAVITY PORTION

CROSS-REFERENCE TO RELATED APPLICATIONS

This application claims priority from Korean Patent Application No. 10-2011-0084060, filed on Aug. 23, 2011, in the Korean Intellectual Property Office, the disclosure of which is incorporated by reference herein in it entirety.

BACKGROUND

1. Field

The present disclosure relates to a terahertz interaction circuit, and more particularly, to a terahertz interaction circuit having a narrow open cavity structure.

2. Description of the Related Art

A terahertz frequency range between a microwave frequency range and an optical frequency range is used in the fields of molecular optics, biophysics, medical science, spectroscopy, or imaging or security. However, there have been few developments in the field of terahertz oscillators or amplifiers for generating terahertz waves due to physical and engineering limitations. Recently, as various new theories and fine processing technologies are introduced, the terahertz oscillators or amplifiers are being developed.

In particular, there has been proposed an interaction circuit for oscillating terahertz waves through the interaction between an electronic beam and an electromagnetic wave in a terahertz oscillator using a vacuum electronic technology. In such an interaction circuit, electric field magnitude and interaction impedance are characteristic factors. As the strength of an electric field magnitude increases, the efficiency of converting the energy of an electronic beam into electromagnetic wave energy is improved. Interaction impedance is a factor in output efficiency and is proportional to the square of the electric field magnitude.

Thus, the electric field magnitude affects the interaction impedance.

SUMMARY

One of more embodiments provide a terahertz interaction circuit having a narrow open cavity structure.

According to an aspect of an embodiment, there is provided a terahertz interaction circuit that includes a waveguide through which electromagnetic waves pass, the waveguide having a folded shape and including a narrow open cavity portion; and an electron beam tunnel through which an electron beam passes, the electron beam tunnel penetrating through the waveguide.

The electron beam tunnel may penetrate through the open cavity portion of the waveguide.

The waveguide may be folded cyclically, each cycle of the waveguide may comprise an open cavity portion, and the electron beam tunnel may penetrate through the open cavity portion of each cycle of the waveguide.

The waveguide may include a first tapered portion connected to one side of the open cavity portion and a second tapered portion connected to the other side of the open cavity portion, each of the first tapered portion and the second tapered portion having a cross section that gradually decreases toward the open cavity portion.

The waveguide may have a rectangular cross section.

The open cavity portion may have a shape that is narrowed along a direction in which the electron beam proceeds as compared to the remaining portions of the waveguide.

The waveguide may have a circular cross section.

The electron beam tunnel may have a rectangular or circular cross section.

Electromagnetic waves of a millimeter wavelength range, a sub-millimeter wavelength range, or a terahertz frequency range may proceed through the waveguide.

The waveguide and the electron beam tunnel may be formed in a block.

The block may be formed of a metal material.

The block may be formed of a non-metal material and inner wall surfaces of the waveguide and the electron beam tunnel are coated with metal.

BRIEF DESCRIPTION OF THE DRAWINGS

The above and/or other aspects will become apparent and more readily appreciated from the following description of the embodiments, taken in conjunction with the accompanying drawings in which:

FIG. 6 illustrates a terahertz interaction circuit including a folded waveguide having a uniform rectangular sectional shape;

DETAILED DESCRIPTION

Figure 1:
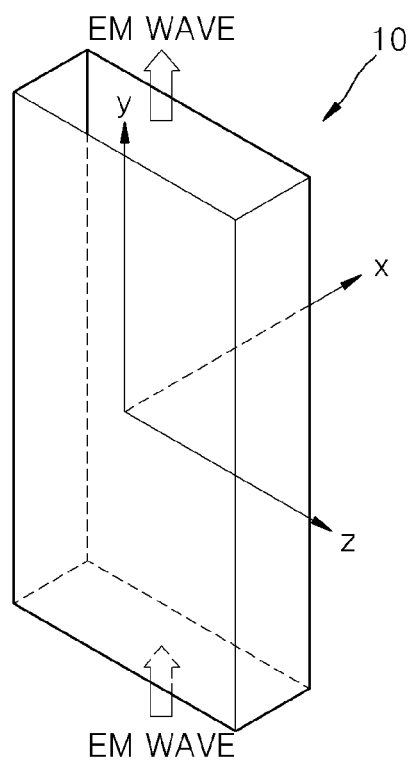
FIG. 1 illustrates a waveguide having a uniform rectangular sectional shape.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Figure 2A:
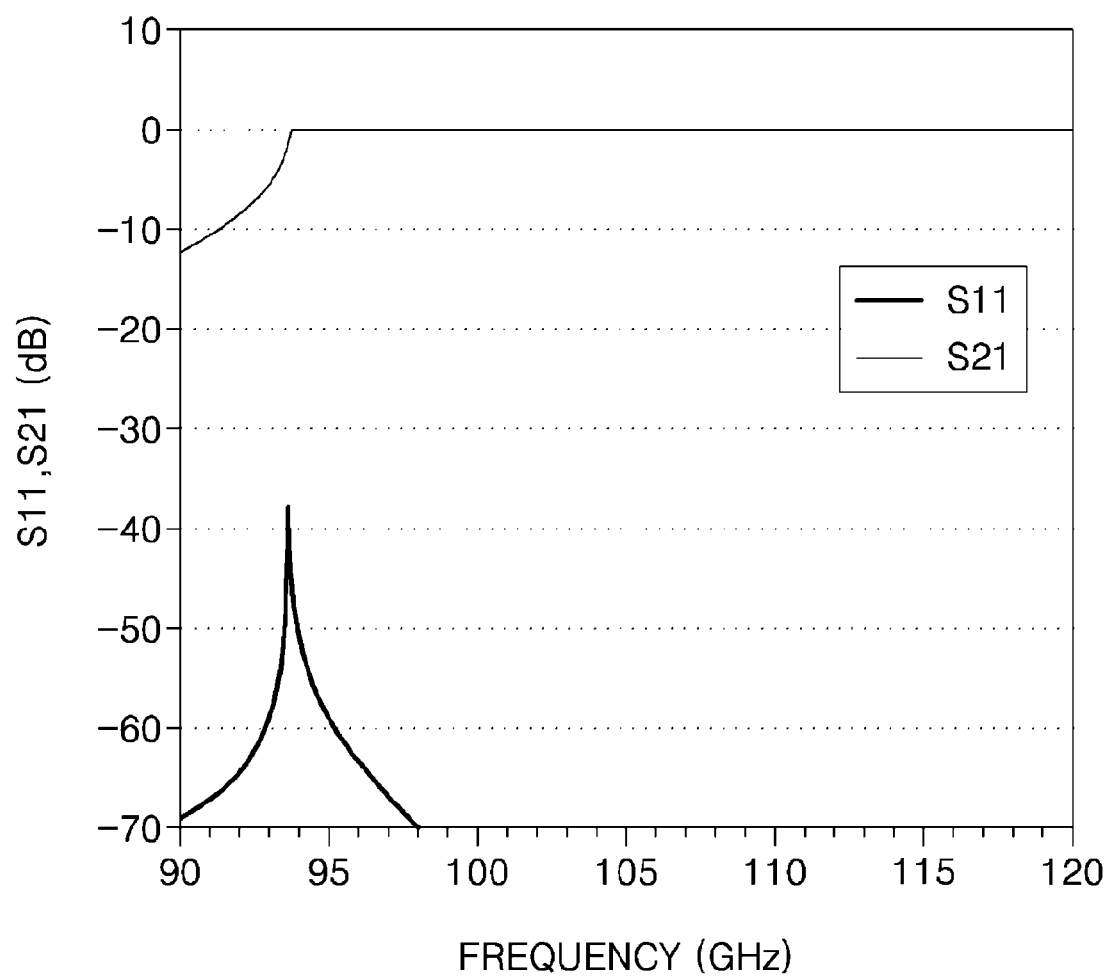
FIG. 2A is a graph showing a result of a simulation of calculating an s-parameter according to a frequency, with respect to the waveguide of FIG. 1.
Figure 2B:
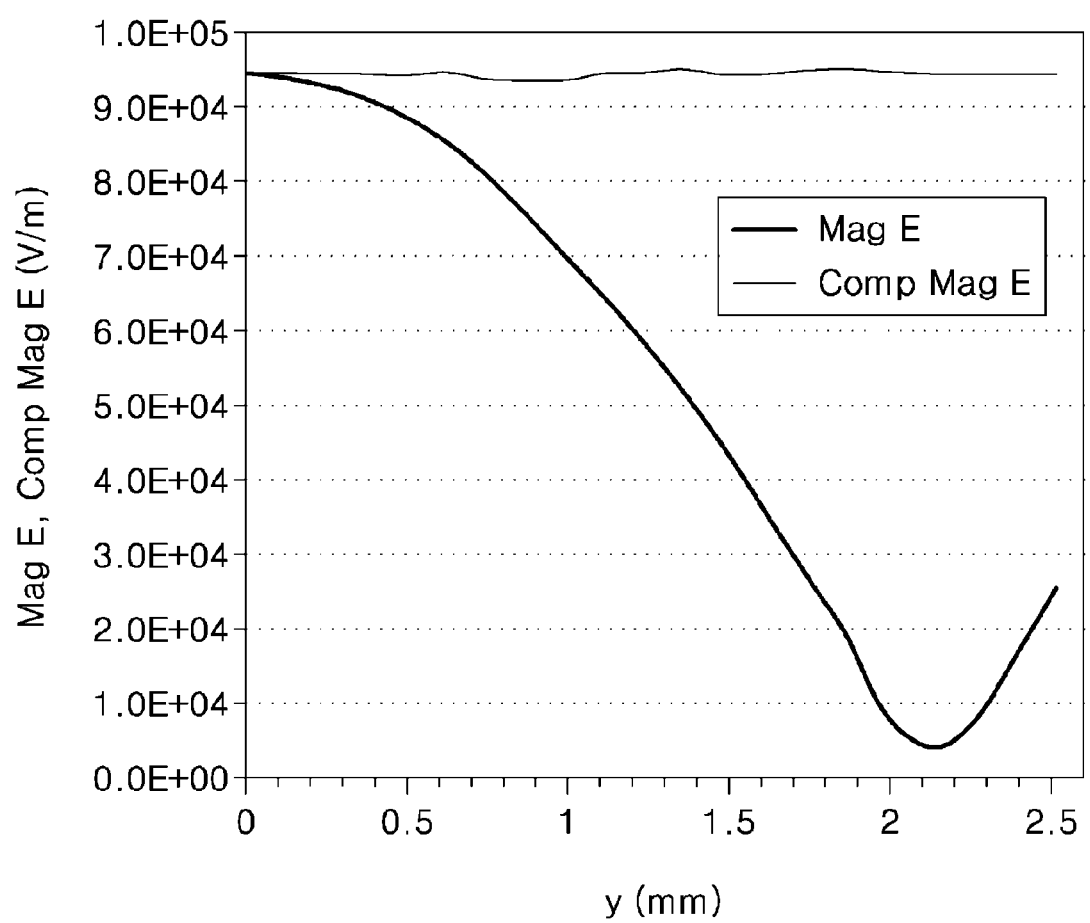
FIG. 2B is a graph showing a result of a simulation of calculating Magnitude E and Complex Magnitude E in y direction, with respect to the waveguide of FIG. 1.
Figure 2C:
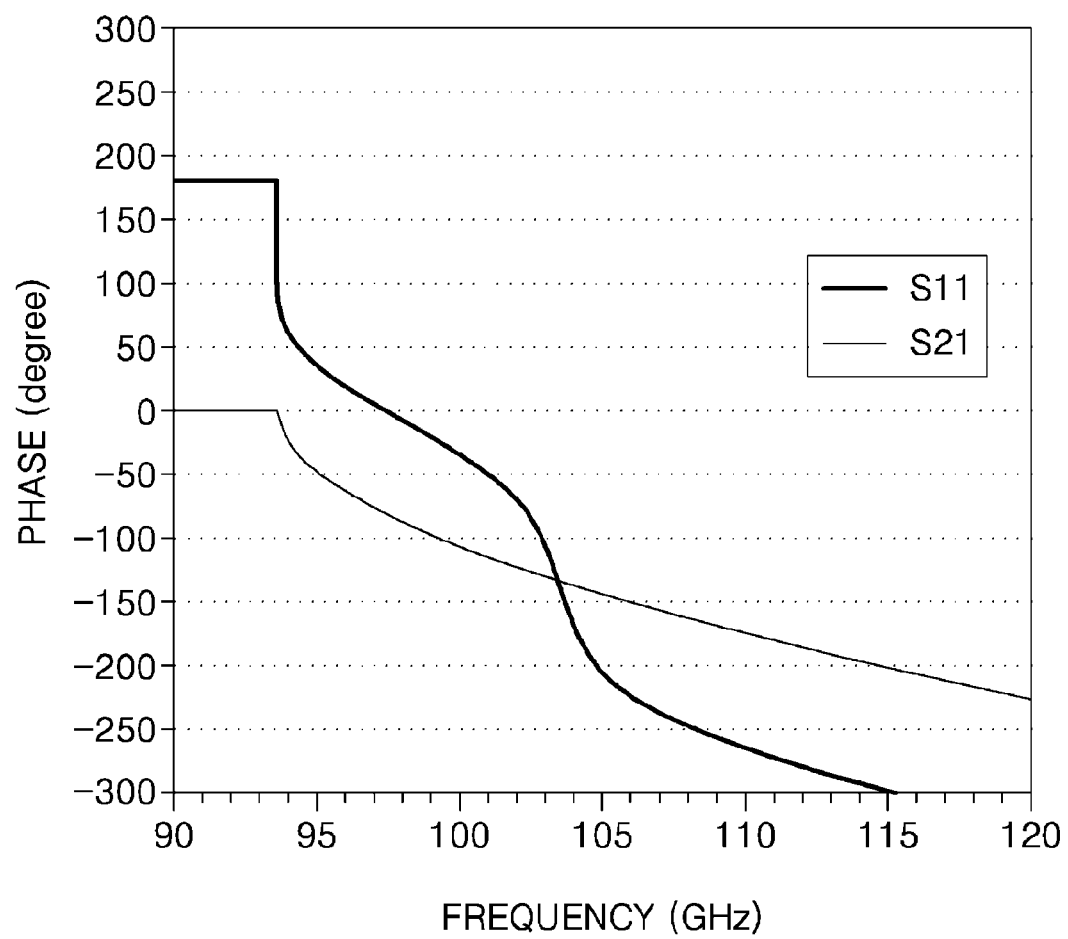
FIG. 2C is a graph showing a result of a simulation of calculating a phase according to a frequency, with respect to the waveguide of FIG. 1.

FIG. 1 illustrates a waveguide 10 having a uniform rectangular sectional shape. FIGS. 2A-2C illustrate results of a simulation calculated when a 100 GHz electromagnetic (EM) wave having a 1 W output is incident on the inside of the waveguide 10 of FIG. 1. In detail, FIG. 2a shows a result of a simulation of an s-parameter according to a frequency. FIG. 2B shows a result of a simulation of calculating Magnitude E and Complex Magnitude E in y direction. In FIG. 2B, Mag E indicates the magnitude of an electric field at a particular time point and is dependent on time, whereas Com Mag E indicates the magnitude of an electric field in which the time dependency is eliminated and represented by a value of a complex magnitude, that is, $|E \cdot E^*|$. FIG. 2C shows a result of a simulation of calculating a phase according to a frequency.

Referring to FIG. 2A, a value of a graph S21 is 0 dB for frequencies over about 93.5 GHz so that it may be seen that a cut-off frequency is about 93.5 GHz. Referring to FIG. 2B, Comp Mag E is the greatest at the central portion of the waveguide 10 and its maximum value is about 0.95E+5 V/m.

Figure 3:
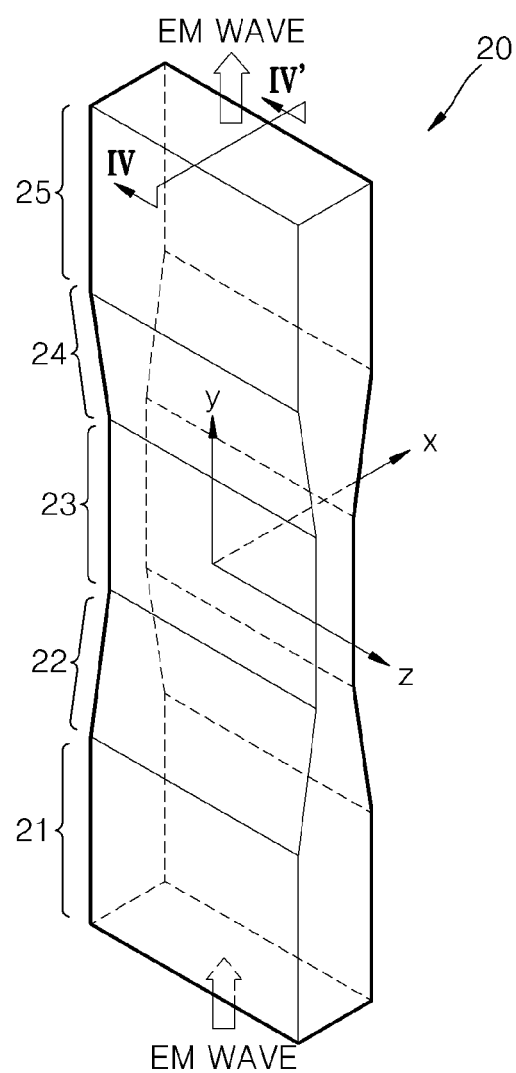
FIG. 3 illustrates a waveguide having a narrow open cavity structure.
Figure 4:
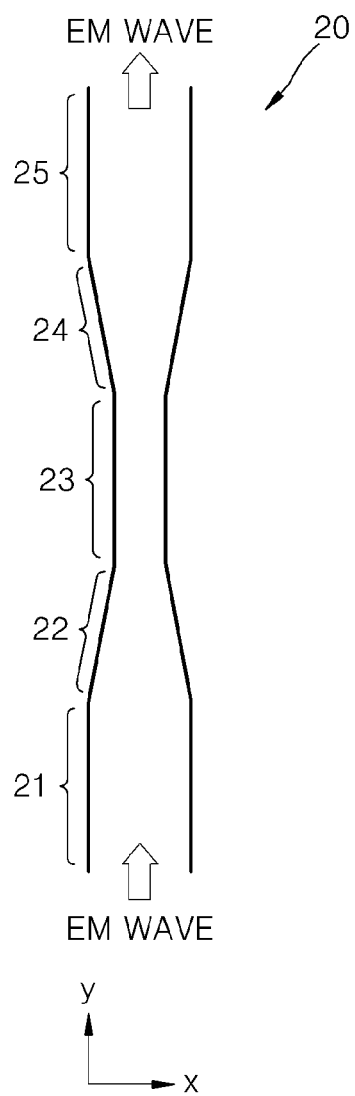
FIG. 4 is a cross sectional view taken along line IV-IV' of FIG. 3.

FIG. 3 illustrates a waveguide 20 having a narrow open cavity structure. FIG. 4 is a cross sectional view taken along line IV-IV' of FIG. 3. Referring to FIGS. 3 and 4, an open cavity portion 23 that is narrower than any other portions is formed in the waveguide 20. In detail, the open cavity portion 23 is formed between an input portion 21 and an output portion 25 to be narrower than the input portion 21 and the output portion 25. In FIGS. 3 and 4, the open cavity portion 23 is more narrow that the input portion 21 and the output portion 25 in the x direction. The input portion 21 and the output portion 25 have uniform sectional areas. The open cavity portion 23 has a uniform sectional area smaller than the input portion 21 and the output portion 25. The input portion 21, the output portion 25, and the open cavity portion 23 may have rectangular sections. A first tapered portion 22 having a sectional area decreasing toward the open cavity portion 23, that is, in the y direction, is formed between the input portion 21 and the open cavity portion 23. A second tapered portion 24 having a sectional area decreasing toward the open cavity portion 23, that is, in -y direction, is formed between the output portion 25 and the open cavity portion 23. The first tapered portion 22 and the second tapered portion 24 may have rectangular sections. The first tapered portion 22 and the second tapered portion 24 communicate with the open cavity portion 23. Thus, in the waveguide 20, electromagnetic waves sequentially pass through the input portion 21, the first tapered portion 22, the open cavity portion 23, the second tapered portion 24, and the output portion 25.

The waveguide 20 having the above-described narrow open cavity structure simultaneously performs a waveguide function and a resonance tube function so that the magnitude of electromagnetic waves passing through the inside of the waveguide 20 may be maximized in the open cavity portion 23. In detail, the magnitude of electromagnetic waves is increased by the first tapered portion 22 and the second tapered portion 24 formed between the input portion 21 and the output portion 25 of the waveguide 20 and simultaneously reflection waves are generated due to an increase in characteristic impedance. The reflection waves concentrate at the open cavity portion 23 located at the central portion of the waveguide 20. As a result, the magnitude of an electric field is increased due to confinement of the electromagnetic waves. Values of characteristic factors of the open cavity portion 23 vary according to inclination angles or shapes of the first tapered portion 22 and the second tapered portion 24.

Figure 5A:
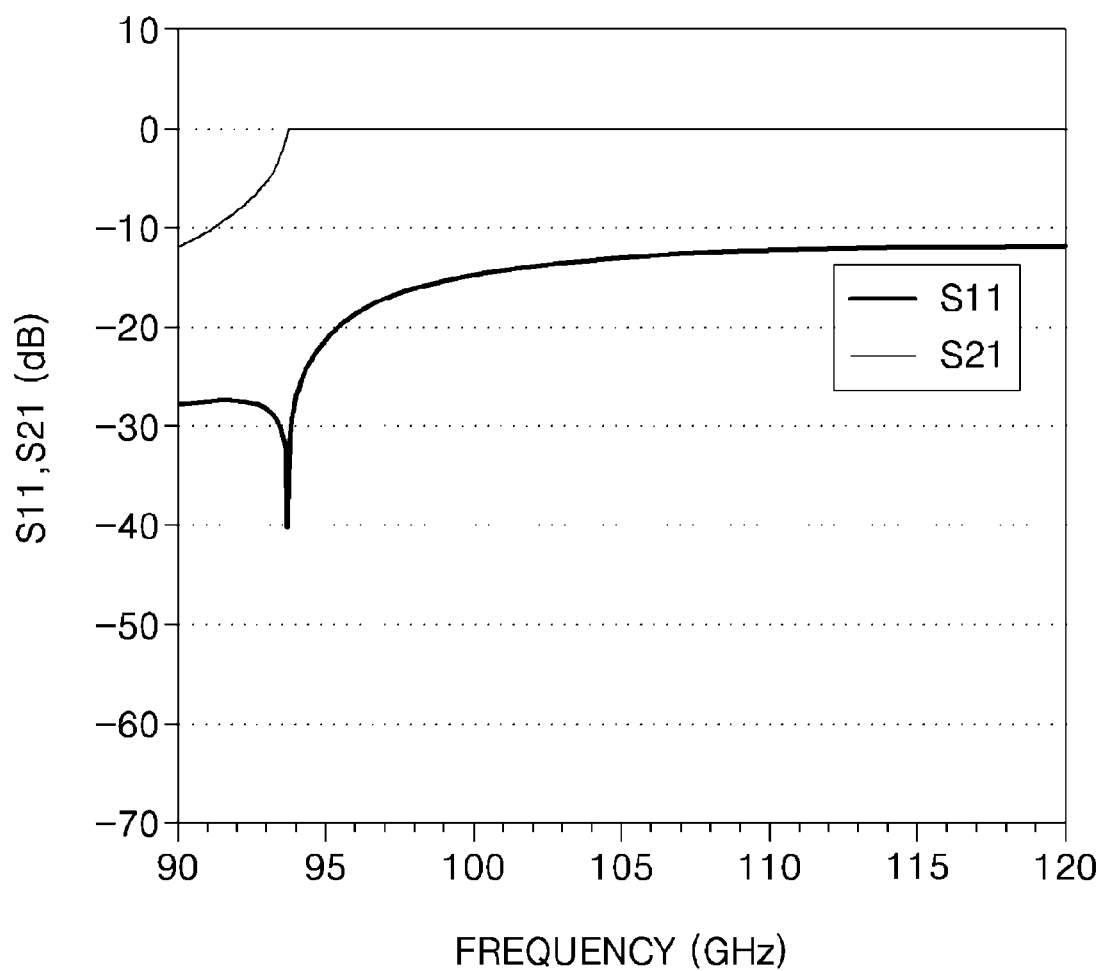
FIG. 5A is a graph showing a result of a simulation of calculating an s-parameter according to a frequency, with respect to the waveguide of FIG. 3.
Figure 5B:
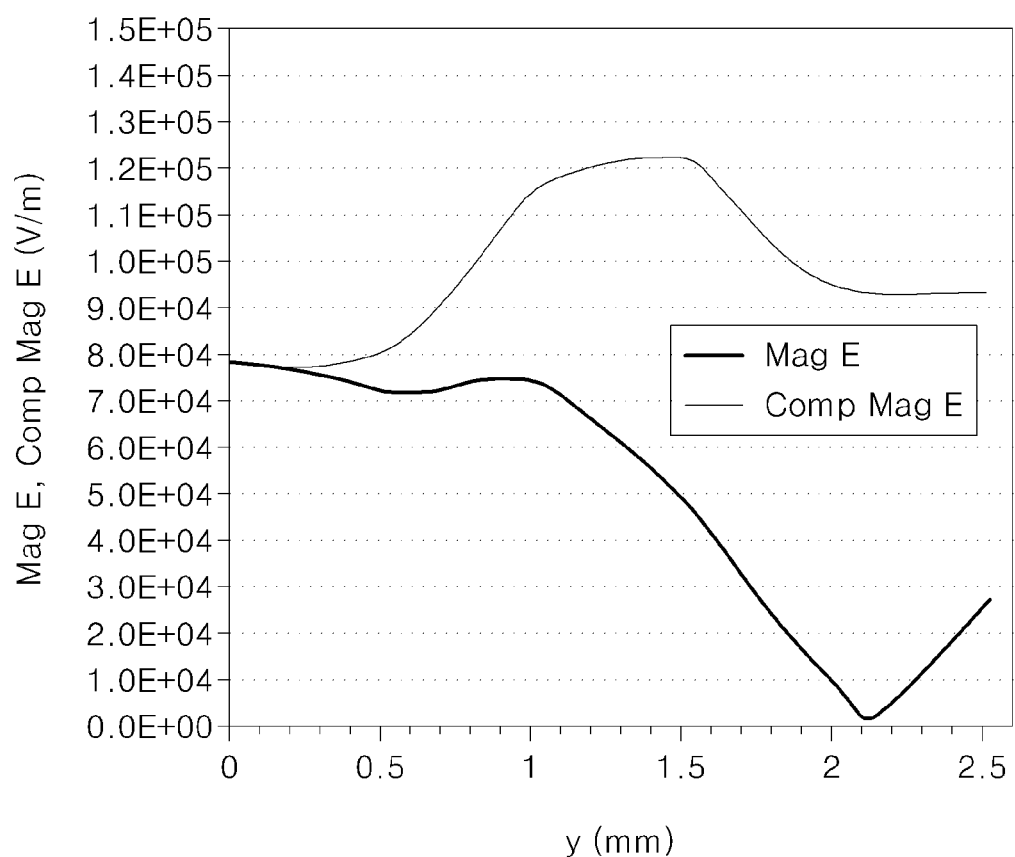
FIG. 5B is a graph showing a result of a simulation of calculating Magnitude E and Complex Magnitude E in the y direction, with respect to the waveguide of FIG. 3.
Figure 5C:
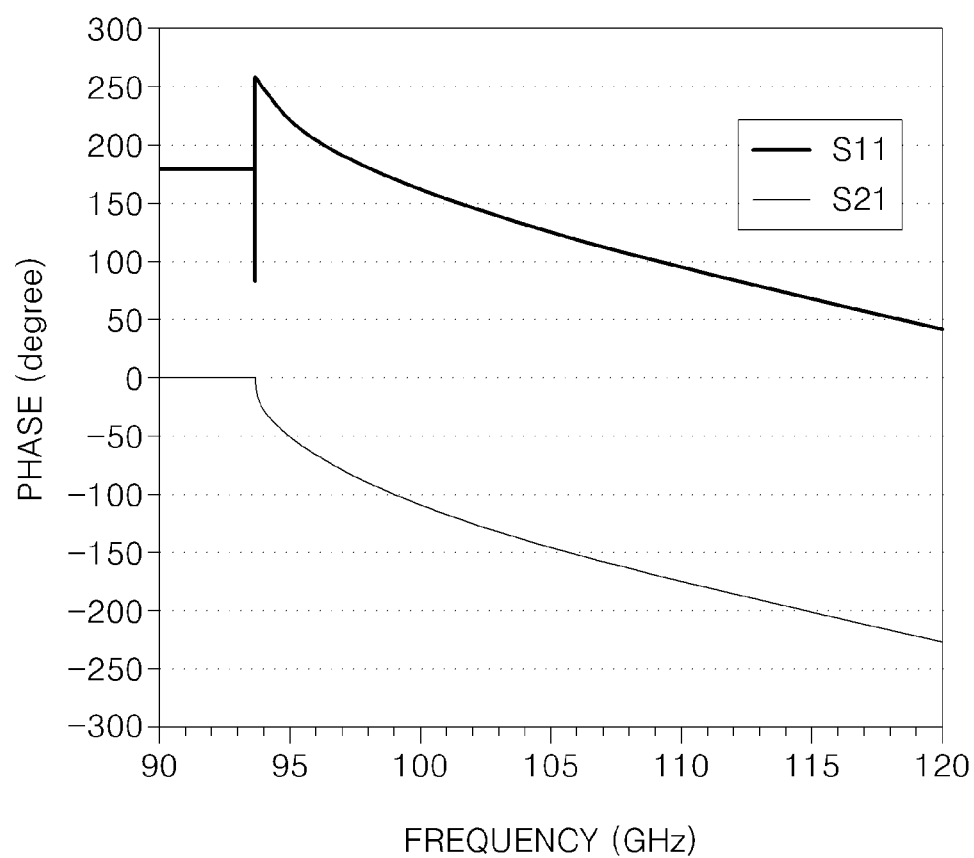
FIG. 5C is a graph showing a result of a simulation of calculating a phase according to a frequency, with respect to the waveguide of FIG. 3.

FIGS. 5A-5C show simulation results calculated when a 100 GHz electromagnetic wave having a 1 W output is incident in the waveguide 20 having a narrow open cavity structure illustrated in FIG. 3. In detail, FIG. 5A is a graph showing a result of a simulation of calculating an s-parameter according to a frequency. FIG. 5B is a graph showing a result of a simulation of calculating Magnitude E and Complex Magnitude E in the y direction. In FIG. 5B, the Mag E indicates the magnitude of an electric field at a particular time point and is dependent on time. The Com Mag E indicates the magnitude of an electric field in which the time dependency is eliminated and represented by a value of a complex magnitude, that is, $|E \cdot E^*|$. FIG. 2C shows a result of a simulation of calculating a phase according to a frequency.

Referring to FIG. 5A, it can be seen that there is no change in a bandwidth compared to a case of the waveguide 10 of FIG. 1 having a uniform rectangular structure. Referring to FIG. 5B, it can be seen that the magnitude of an electric field, that is, the maximum value of the Comp Mag E, in the open cavity portion 23 is increased by about 1.28 times compared to the waveguide 10 of FIG. 1 having a uniform rectangular structure. When the waveguide 20 having a narrow open cavity structure is adopted in a terahertz interaction circuit, the magnitude of an electric field may be increased.

FIG. 6 illustrates a terahertz interaction circuit including a folded waveguide 110 having a uniform rectangular sectional shape. Referring to FIG. 6, the terahertz interaction circuit includes the waveguide 110 having a folded shape and an electron beam tunnel 120 provided to penetrate the waveguide 110. The waveguide 110 and the electron beam tunnel 120 may be formed in a block 100 formed of a predetermined material. The waveguide 110 may have a cyclically folded shape, through which electromagnetic waves pass. The waveguide 110 is folded to effectively reduce the speed of the electromagnetic waves. In a general electromagnetic wave interaction circuit, the speed of electromagnetic waves proceeding in a waveguide is much faster than that of the electron beam. Thus, by forming the waveguide 110 in a folded shape, the speed of the electromagnetic waves interacting with the electron beam may be effectively reduced. The waveguide 110 having a folded shape has a simple structure and a relatively wide operation frequency range and thus is widely used for oscillation or amplification of the electromagnetic waves. The cross section of the waveguide 110 may have a uniform shape, for example, a uniform rectangular shape. The electron beam tunnel 120 that is a path through which electrons pass is provided to penetrate the waveguide 110. In detail, the electron beam tunnel 120 is formed to cyclically penetrate the waveguide 110 having a folded shape. The cross section of the electron beam tunnel 120 may have, for example, a rectangular shape.

Figure 7A:
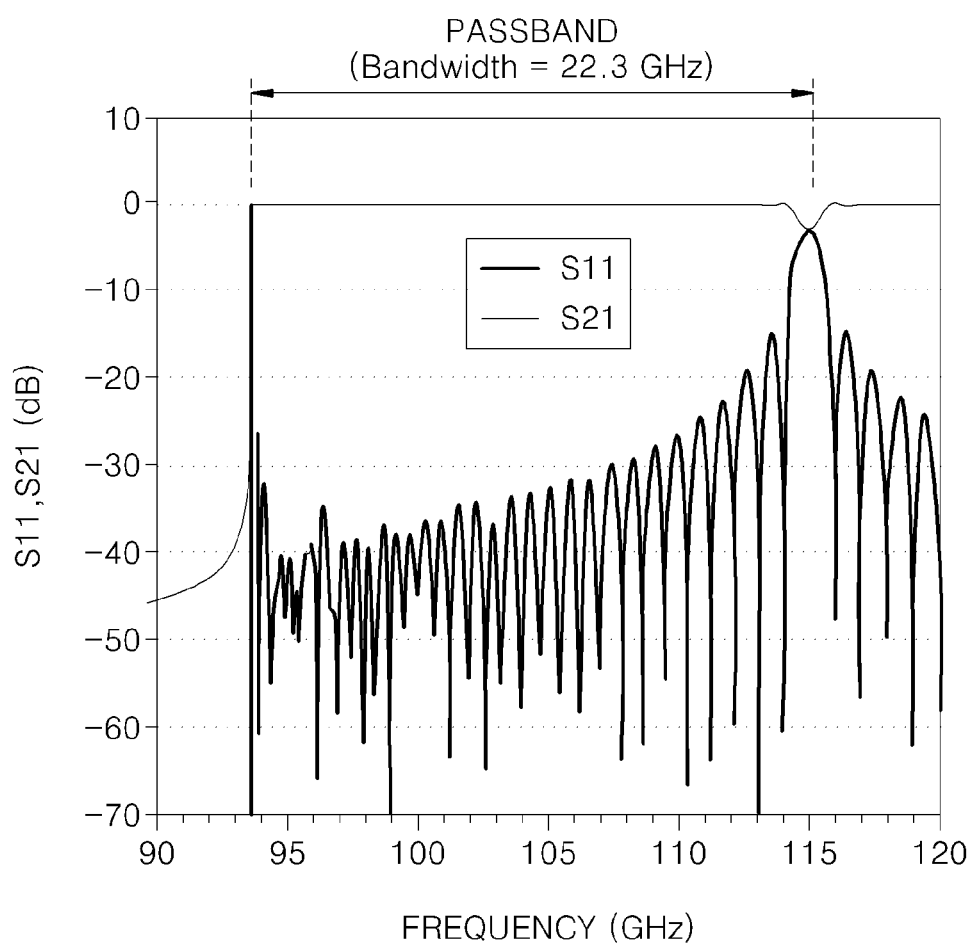
FIG. 7A is a graph showing a result of a simulation of calculating an s-parameter according to a frequency, with respect to the terahertz interaction circuit of FIG. 6.
Figure 7B:
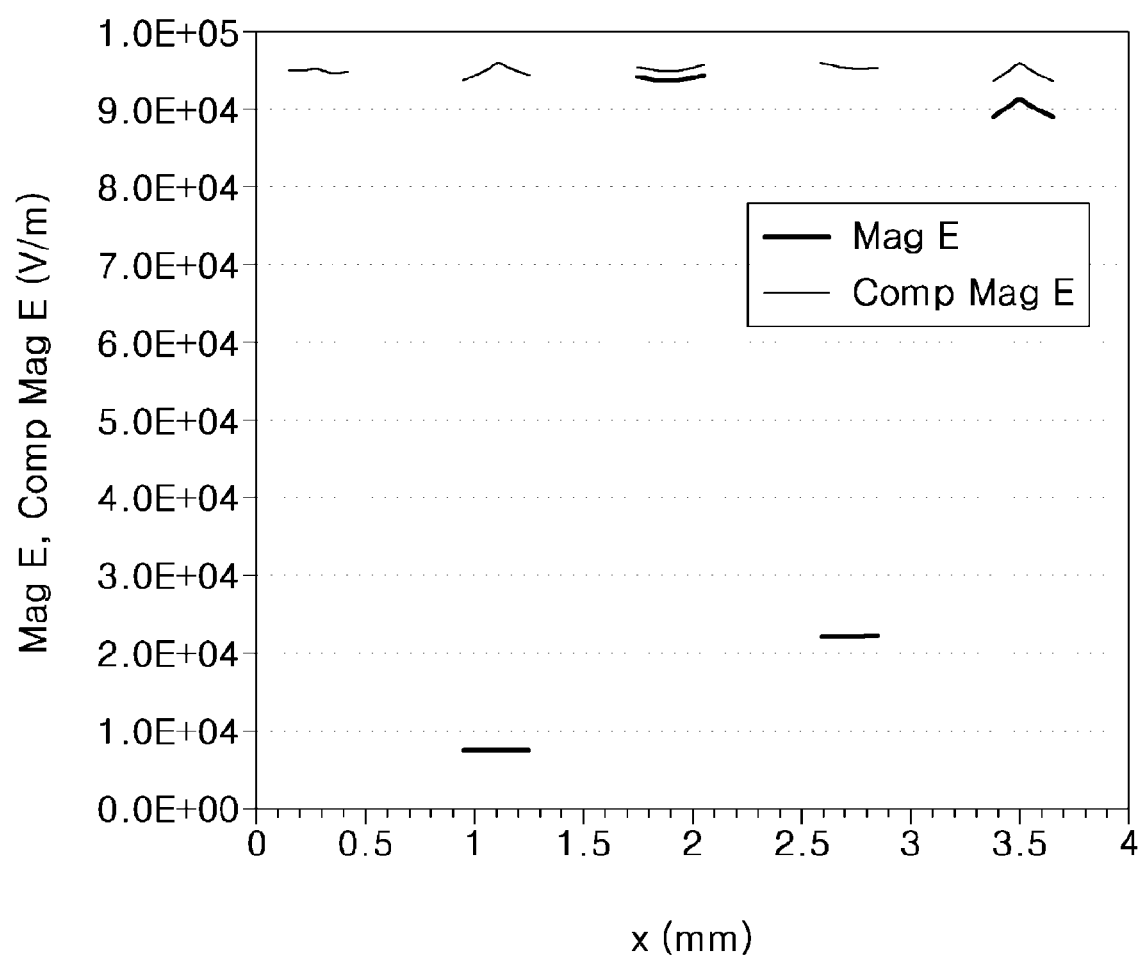
FIG. 7B is a graph showing a result of a simulation of calculating Magnitude E and Complex Magnitude E in x direction, with respect to the terahertz interaction circuit of FIG. 6.

FIGS. 7A and 7B show simulation results calculated when a 100 GHz electromagnetic wave having a 1 W output is incident in the waveguide 110 in the terahertz interaction circuit of FIG. 6. In detail, FIG. 7A is a graph showing a result of a simulation of calculating an s-parameter according to a frequency. FIG. 7B is a graph showing a result of a simulation of calculating Magnitude E and Complex Magnitude E in the x direction. In FIG. 7B, the Mag E indicates the magnitude of an electric field at a particular time point and is dependent on time. The Com Mag E indicates the magnitude of an electric field in which the time dependency is eliminated and represented by a value of complex magnitude, that is, |E·E*|.

Referring to FIG. 7A, a bandwidth is about 22.3 GHz, which corresponds to about 22.3% of the input frequency of 100 GHz. Referring to FIG. 7B, it can be seen that the magnitude of an electric field, that is, the maximum value of the Comp Mag E, is about 0.95E+4 V/m. The terahertz interaction circuit including a waveguide having a folded shape and a uniform sectional shape exhibits a simple structure and a simple condition of interaction between an electron beam and electromagnetic waves, that is, the phase speed of electromagnetic waves and the speed of electrons, and also a wide bandwidth. However, due to a relatively low magnitude of an electric field, the interaction between the electron beam and the electromagnetic waves is weak and also the interaction impedance value is decreased.

Figure 8:
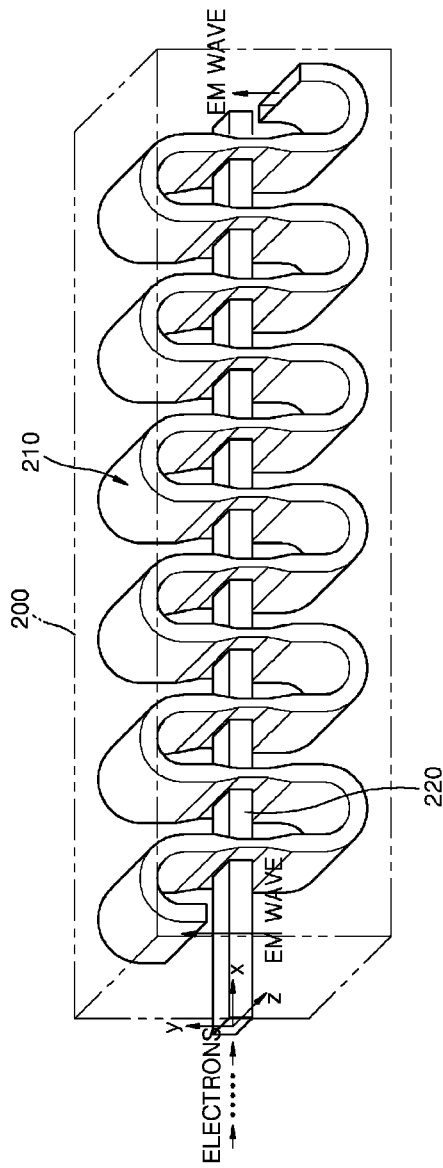
FIG. 8 illustrates a terahertz interaction circuit including a folded waveguide having a narrow open cavity structure, according to an exemplary embodiment.
Figure 9:
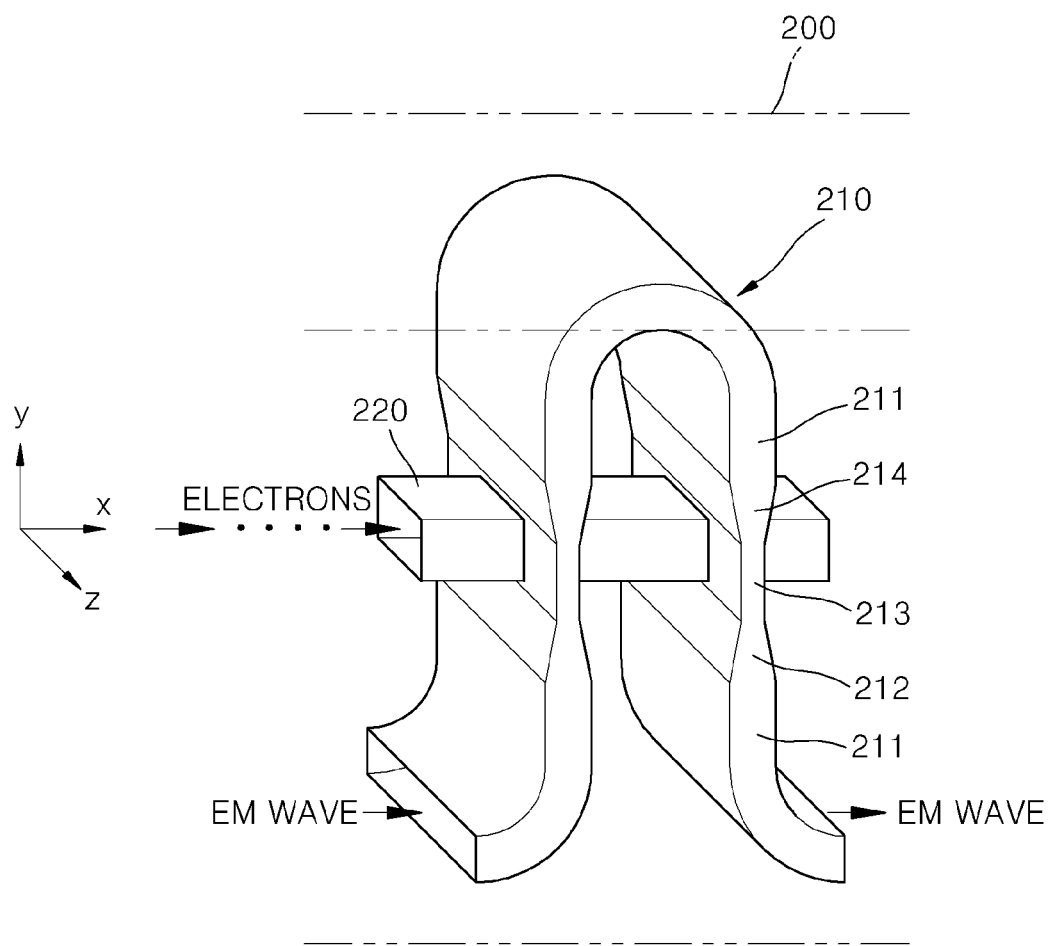
FIG. 9 is a partially enlarged view of the terahertz interaction circuit of FIG. 8.

FIG. 8 illustrates a terahertz interaction circuit including a folded waveguide 210 having a narrow open cavity structure, according to an exemplary embodiment. FIG. 9 is a partially enlarged view of the terahertz interaction circuit of FIG. 8.

Referring to FIGS. 8 and 9, the terahertz interaction circuit includes the waveguide 210 having a folded shape and an electron beam tunnel 220 provided to penetrate the waveguide 210. The waveguide 210 and the electron beam tunnel 220 may be formed in a block 200 formed of a metal material such as copper (Cu), silver (Ag), gold (Au), stainless steel, or the like. Alternatively, the block 200 may be formed of a non-metal material such as silicon or the like. In the case that the block 200 is formed of a non-metal material, the inner surfaces of the waveguide 210 and the electron beam tunnel 220 may be coated with a metal layer.

The waveguide 210, through which electromagnetic waves pass, may have a cyclically folded shape. As described above, the waveguide 110 is folded to effectively reduce the speed of the electromagnetic waves. In a general electromagnetic wave interaction circuit, the speed of the electromagnetic waves proceeding in a waveguide is much faster than that of the electron beam. Thus, by forming the waveguide 210 in a folded shape, the speed of the electromagnetic waves interacting with the electron beam may be effectively reduced. Electromagnetic waves, for example, in a millimeter wavelength range, a sub-millimeter wavelength range, or a terahertz frequency range may proceed in the waveguide 210.

In the embodiment, the waveguide 210 includes an open cavity portion 213 (see FIG. 9). The open cavity portion 213 has a shape that is narrower than the other portions of the waveguide 210. In detail, the waveguide 210 may include a body portion 211 having a uniform cross section, at least one open cavity portion 213 having a uniform cross section smaller than the body portion 211, and at least a first tapered portion 212 and a second tapered portion 214 connecting the body portion 211 and the open cavity portion 213. The body portion 211 may have, for example, a rectangular sectional shape. However, the present invention is not limited thereto and the body portion 211 may have circular or various other sectional shapes. The open cavity portion 213 is narrower than the body portion 211 and may have, for example, a rectangular sectional shape. In this case, the open cavity portion 213, as illustrated in FIG. 9, may have a structure of being narrow along a direction in which the electron beam proceeds, that is, in the x direction. Alternatively, the at least one open cavity portion 213 may be cyclically formed along the waveguide 210 as illustrated in FIG. 8. The open cavity portion 213 may have various sectional shapes such as a rectangle, a circle, or the like.

The first tapered portion 212 is a path connecting the body portion 211 and one end of the open cavity portion 213 and has a shape in which a cross section gradually decreases toward the open cavity portion 213, that is, in the y direction. The second tapered portion 214 is a path connecting the other end of the open cavity portion 213 and the body portion 211 and has a shape in which a cross section gradually decreases toward the open cavity portion 213, that is, in the -y direction. The first tapered portion 212 and the second tapered portion 214 may have, for example, a rectangular sectional shape. However, the present invention is not limited thereto and the first tapered portion 212 and the second tapered portion 214 may have circular or various other sectional shapes. FIG. 9 illustrates that inclined surfaces of the first tapered portion 212 and the second tapered portion 214 are linear. However, the present invention is not limited thereto and the inclined surfaces of the first tapered portion 212 and the second tapered portion 214 may be curved. In such a case, the curved shape may include, for example, a Chebychev polynomials curve shape or a Klopfenstein curve shape.

The electron beam tunnel 220 is a path through which electrons pass and is provided to penetrate the waveguide 210 in the block 200. That is, the electron beam tunnel 220 cyclically penetrates through the waveguide 210 having a folded shape. In detail, the electron beam tunnel 220 may penetrate through the open cavity portion 213 of the waveguide 210.

In the terahertz interaction circuit having the above structure, since the open cavity portion 213 that is narrow in the direction in which an electron beam proceeds, that is, in the x direction, is formed in the waveguide 210, the magnitude of an electric field may be increased and the influence on the flow of electromagnetic waves may be minimized so that the interaction between the electron beam and the electromagnetic waves may be more efficiently performed. As described above, since the waveguide 210 having a narrow open cavity structure may simultaneously perform a waveguide function and a resonance tube function, the magnitude of electromagnetic waves passing through the inside of the waveguide 210 may be maximized in the open cavity portion 223. In detail, the magnitude of electromagnetic waves is increased due to the inclination of the first tapered portion 212 and the second tapered portion 214 formed in the waveguide 210 and simultaneously reflection waves are generated due to an increase in characteristic impedance. The reflection waves concentrate at the open cavity portion 213, that is, a narrow portion of the waveguide 210, so that the magnitude of an electric field in the open cavity portion 213 is increased. As the magnitude of an electric field increases, the interaction impedance increases accordingly. As a result, the interaction between the electromagnetic waves and the electron beam are performed efficiently. When the inclination angles of the first tapered portion 212 and the second tapered portion 214 are low, a reflectance of the reflection waves, that is, a reflectance of S11, decreases so that the interaction between the electromagnetic waves and the electron beam may be performed more effectively.

Figure 10A:
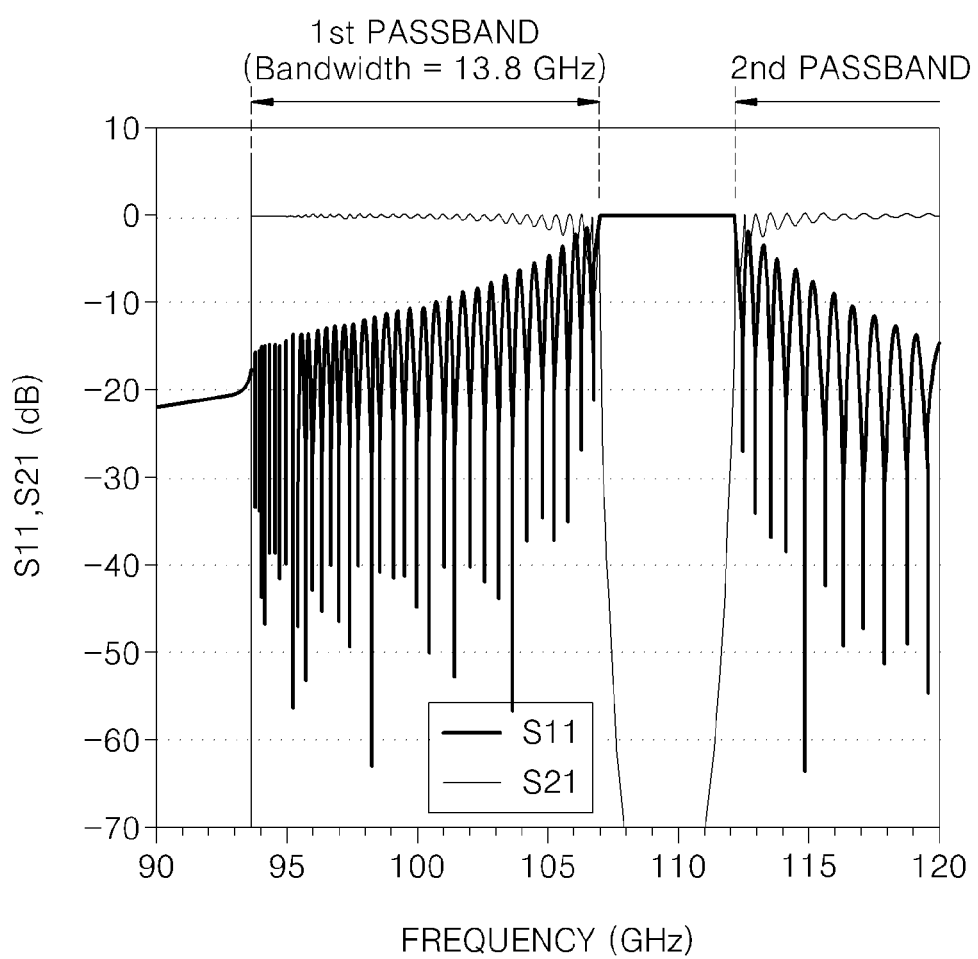
FIG. 10A is a graph showing a result of a simulation of calculating an s-parameter according to a frequency, with respect to the terahertz interaction circuit of FIG. 8.
Figure 10B:
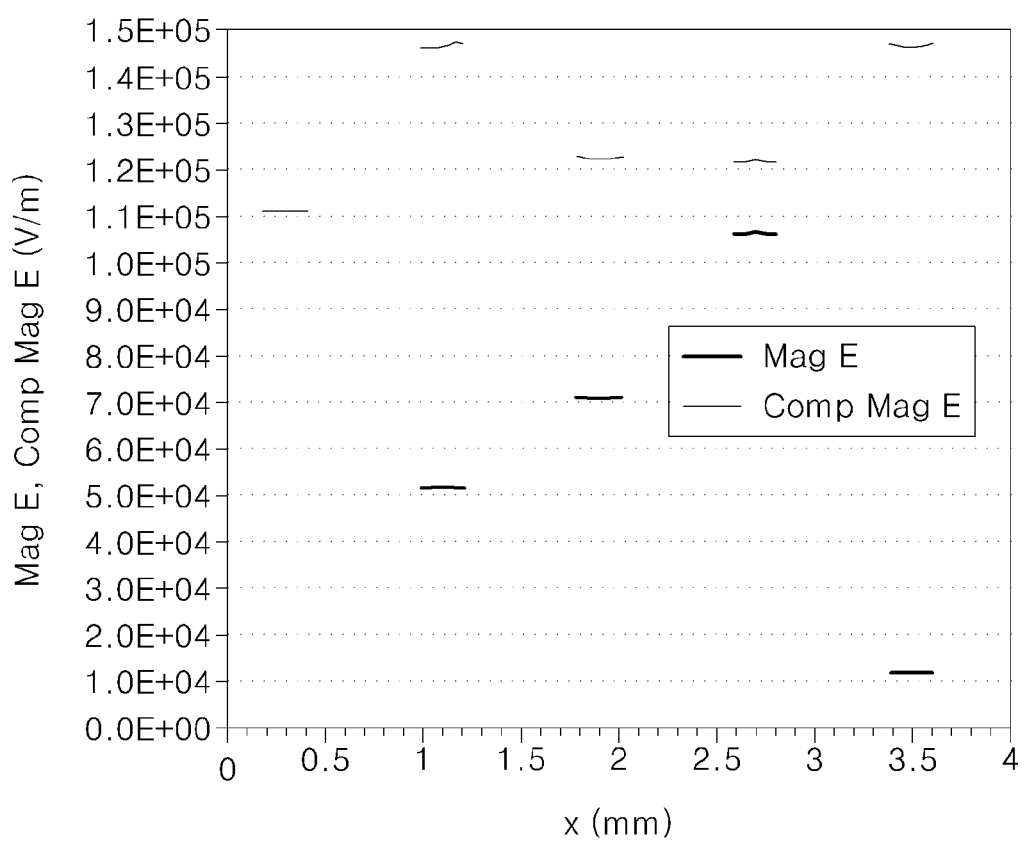
FIG. 10B is a graph showing a result of a simulation of calculating Magnitude E and Complex Magnitude E in the x direction, with respect to the terahertz interaction circuit of FIG. 8.

FIGS. 10A and 10B are graphs showing results of simulations calculated when a 100 GHz electromagnetic wave having a 1 W output is incident on the inside of the waveguide 210 in the terahertz interaction circuit of FIG. 8. In detail, FIG. 10A illustrates a result of a simulation of calculating an s-parameter according to a frequency, and FIG. 10B illustrates a result of a simulation of calculating Magnitude E and Complex Magnitude E in the x direction. In FIG. 10B, the Mag E indicates the magnitude of an electric field at a particular time point and is dependent on time, whereas Com Mag E indicates the magnitude of an electric field in which the time dependency is eliminated and represented by a value of complex magnitude, that is, |E·E*|.

Referring to FIG. 10A, a bandwidth is about 13.8 GHz, which corresponds to about 13.8% of an input frequency of 100 GHz. Thus, it can be seen that the bandwidth is slightly decreased compared to the terahertz interaction circuit including the waveguide 110 of FIG. 6. However, since a second passband is formed at a position close to a first passband, not only the first passband but also the second passband may be used so that a frequency band may be extended. Referring to FIG. 10B, the magnitude of an electric field at the open cavity portion 213 of the waveguide 210, that is, the maximum value of the Comp Mag E, is increased by about 1.54 times compared to the terahertz interaction circuit including the waveguide 110 of a folded structure having a uniform cross section of FIG. 6. Thus, it can be seen that, in the terahertz interaction circuit according to the present exemplary embodiment, the magnitude of an electric field is increased compared to the terahertz interaction circuit including the waveguide 110 having a uniform cross section.

As described above, according to exemplary embodiments, since a narrow open cavity structure is formed in the waveguide and the electron beam and the electromagnetic waves interact in the open cavity structure, the magnitude of an electric field may be increased without interfering with the flow of the electromagnetic waves. Also, since interaction impedance increases, the interaction between the electron beam and the electromagnetic waves may be efficiently performed. Furthermore, since the second passband is formed close to the first passband, a large frequency range may be secured.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A terahertz interaction circuit comprising:
    a waveguide through which electromagnetic waves pass and having a folded shape and , the waveguide comprising a narrow open cavity portion; and
    an electron beam tunnel through which an electron beam passes, the electron beam tunnel penetrating through the waveguide,
    wherein the waveguide further comprises:
    a first tapered portion connected to one side of the narrow open cavity portion; and
    a second tapered portion connected to the other side of the narrow open cavity portion, each of the first tapered portion and the second tapered portion having a cross section that gradually decreases toward the narrow open cavity portion.

2. The terahertz interaction circuit of claim 1, wherein the electron beam tunnel penetrates through the narrow open cavity portion of the waveguide.

3. The terahertz interaction circuit of claim 1, wherein the waveguide is folded cyclically, each cycle of the waveguide comprises an open cavity portion, and the electron beam tunnel penetrates through the open cavity portion of each cycle of the waveguide.

4. The terahertz interaction circuit of claim 1, wherein a surface of the first tapered portion is inclined toward the narrow open cavity portion, a surface of the second tapered portion is inclined toward the narrow open cavity portion, and the inclined surfaces of the first and second tapered portions are linear or curved.

5. The terahertz interaction circuit of claim 1, wherein the narrow open cavity portion has a uniform cross section.

6. The terahertz interaction circuit of claim 1, wherein the waveguide has a rectangular cross section.

7. The terahertz interaction circuit of claim 6, wherein the narrow open cavity portion has a shape that is narrowed along a direction in which the electron beam proceeds as compared to remaining portions of the waveguide.

8. The terahertz interaction circuit of claim 1, wherein the waveguide has a circular cross section.

9. The terahertz interaction circuit of claim 1, wherein the electron beam tunnel has a rectangular or circular cross section.

10. The terahertz interaction circuit of claim 1, wherein electromagnetic waves of a millimeter wavelength range, a sub-millimeter wavelength range, or a terahertz frequency range proceed through the waveguide.

11. The terahertz interaction circuit of claim 1, wherein the waveguide and the electron beam tunnel are formed in a block.

12. The terahertz interaction circuit of claim 11, wherein the block is formed of a metal material.

13. The terahertz interaction circuit of claim 11, wherein the block is formed of a non-metal material and inner wall surfaces of the waveguide and the electron beam tunnel are coated with a metal.

14. A terahertz interaction circuit comprising:
    a waveguide comprising a plurality of folded portions and a plurality of straight portions connecting together the folded portions, each of the straight portions comprising an open cavity portion having a cross-sectional area smaller than remaining portions of the waveguide; and
    an electron beam tunnel which passes through the open cavity portions,
    wherein each of the straight portions further comprises a first tapered portion connected to one end of the open cavity portion, and a second tapered portion connected to another end of the open cavity portion, each of the first tapered portion and the second tapered portion having a cross section that gradually decreases toward the open cavity portion.

15. The terahertz interaction circuit of claim 14, wherein the ends of the first tapered portion and the second tapered portion opposite the ends connected to the open cavity portion are connected to respective ones of the folded portions.

* * * * *